United States Patent [19]

Gavello

[11] Plant 4,918

[45] Nov. 2, 1982

[54] ESCALLONIA PLANT NAMED 'ESCALLONLA TERRI'

[76] Inventor: Louis E. Gavello, 3436 Maricopa Ave., Richmond, Calif. 94804

[21] Appl. No.: 243,827

[22] Filed: Mar. 16, 1981

[51] Int. Cl.[3] ..... A01H 5/00

[52] U.S. Cl. ..... Plt./54

[58] Field of Search ..... Plt./54

*Primary Examiner*—James R. Feyrer

*Attorney, Agent, or Firm*—Manfred M. Warren; Robert B. Chickering; Glen R. Grunewald

[57] ABSTRACT

A new and distinct variety of Escallonia plant characterized by it being compact to a height of approximately three feet and a spread of approximately six feet, with large leaves from 35 to 50 mm long on petrols 1 to 5 mm long, and with profuse blossoms held in secund, pyramidal panicles 4 to 6 cm high by 4 to 6 cm wide, each panicle numbering about 20 flowers.

2 Drawing Figures

My invention relates to a new and distinct variety of Escallonia plant which was discovered by me about 4 years ago, as a chance seedling in a garden near the Hall Of Flowers, located in Golden Gate Park, San Francisco. I have named this plant Escallonia Terri.

The accompanying picture shows in separate views, a typical bush of my new variety of Escallonia plant as derived from said seedling, a number of racemes on a branch, and specimens of individual leaves, all depicted in color as nearly true as it is reasonably possible to make the same in a color illustration of this character.

The following is a detailed description of my new variety, with color terminology in accordance with Maerz and Paul, a Dictionary of Color, 2nd Edition, 1950.

SPECIES

This Escallonia plant has the characteristics of Escallonia Macrantha and it is believed to be a sport of that species.

REPRODUCTION

The plant is asexually reproduced from cuttings.

FORM

The new shrub when planted in full sun, grows to a height of approximately 3 feet, attains a spread of approximately 6 feet, and maintains compactness with large leaves and profuse blossoms.

GROWTH RATE AND WINTER HARDINESS

From two-inch cuttings the plants grow to a height of three feet in four years. After four years the spread is about six feet. Plants have survived moderate frosts and light freezes, to about 27° F. at the production site and the surrounding area.

FOLIAGE

The foliage is chrome green as identified by Plate 24, P71, Sect.L-12. The leaf is broadly elliptic to broadly obovate. Blades are from 35 to 50 mm long on petroles 1–5 mm long.

The texture of the leaf is shiny and glabrous on its upper surface, slightly roughened beneath with scattered, blackish tubercles.

The midrib is prominent and continuous from base to tip, lateral veins being also prominent and anastomosing at margins, the margins being serrate with 6 to 9 callose-tipped teeth per cm.

The leaf arrangement is alternate.

GLANDS AND LEAF PUBESENCE

The leaves are shiny and without pubescence on upper surfaces. The lower surfaces of the leaves are paler green than the upper surfaces, lack hairs, but have minute glandular tubercles scattered over them at a density of about 25 to 40 per square centimeter.

FLOWER CLUSTERS

The flowers are held in secund, pyramidal panicles 4 to 6 cm high by 4 to 6 cm wide, terminal at ends of branches. Each panicle numbers about 20 flowers.

Individual pedicles arch so that individual flowers are somewhat pendulous.

FLOWER FRAGRANCE AND BLOOMING DATES

The flowers have no characteristic odor. At the production site blooming begins in May and continues until the first frost. The most prolific blooming is between May and August.

FLORETS

Individuals florets are borne on bracteolate pedicels 1–4 mm long; the calyx measures 6–9 mm. at greatest diameter; the petals number 5, each with an ovate blade that measures 5–7 mm. long at the end of a broad claw that measures 9–11 mm. long. The petal color is Rose as identified by Plate 50, P.123, Sect.L-6.

FILAMENTS AND ANTHERS

The stamens number five each with a slender filament 8 to 9 mm. long and bearing an elongate anther 4 mm. long.

STYLES AND STIGMAS

The solitary styles are white and are 8 to 10 millimeters long. At their apex they bear a green, weakly bilobed, depressed-capitate stigma that is 1.5 to 2 millimeters in diameter.

Having described and illustrated my new variety of Escallonia plant, I claim:

1. A new and distinct variety of Escallonia plant substantially as illustrated and described.

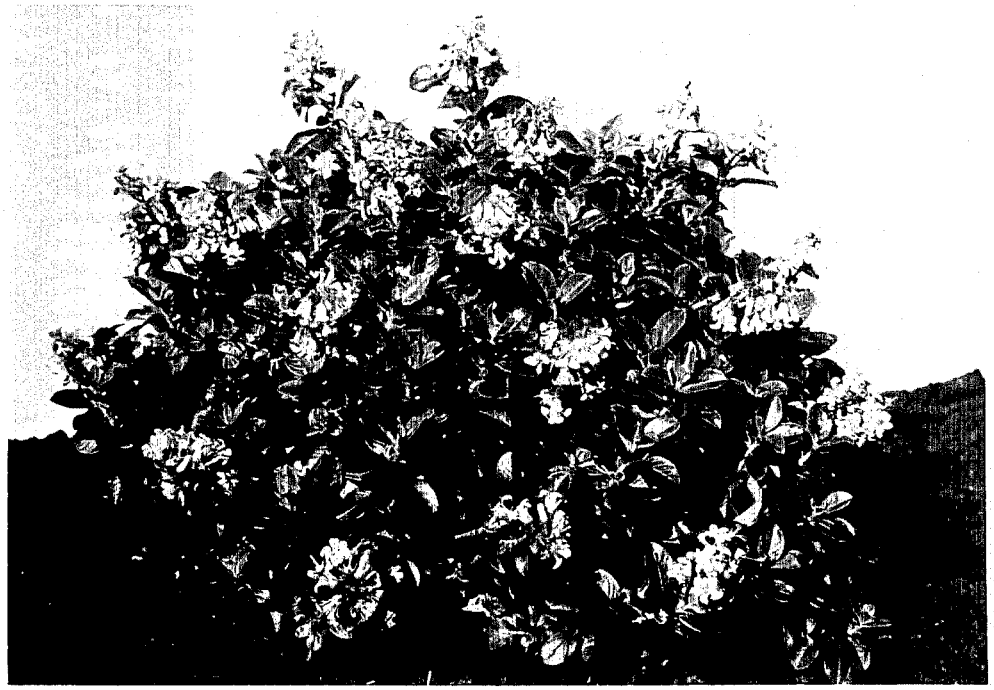
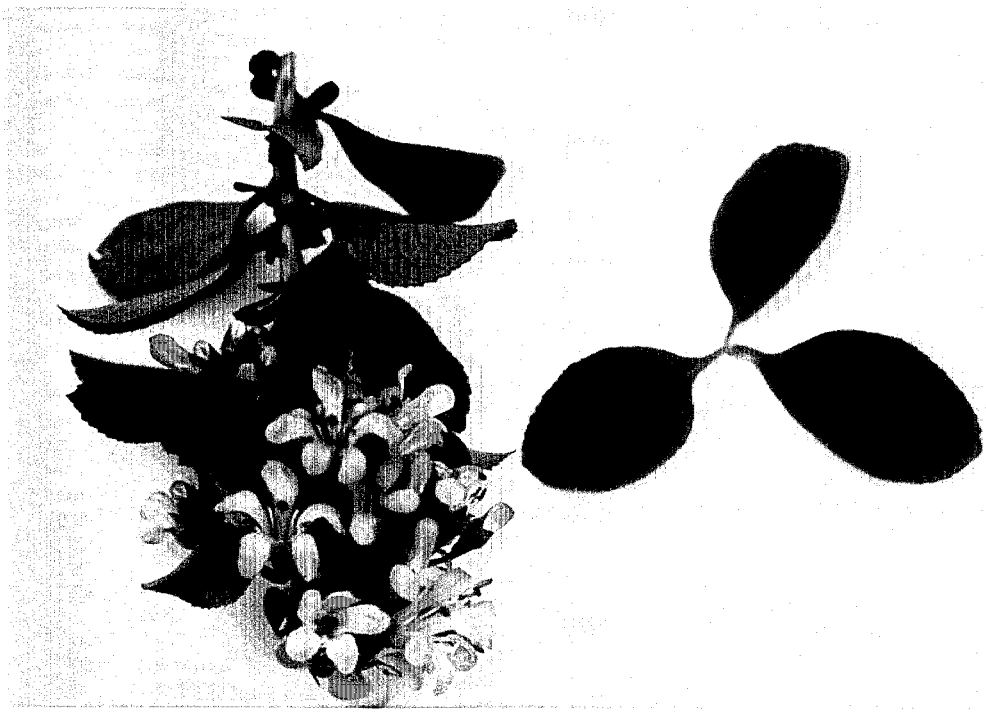

* * * * *